US009326838B1

(12) United States Patent
Kenny

(10) Patent No.: US 9,326,838 B1
(45) Date of Patent: May 3, 2016

(54) FISH DNA SAMPLER

(71) Applicant: The North Umpqua Foundation, Roseburg, OR (US)

(72) Inventor: Garry Robert Kenny, West Linn, OR (US)

(73) Assignee: The North Umpqua Foundation, Roseburg, OR (US)

( * ) Notice: Subject to any disclaimer, the term of this patent is extended or adjusted under 35 U.S.C. 154(b) by 0 days.

(21) Appl. No.: 14/521,518

(22) Filed: Oct. 23, 2014

(51) Int. Cl.
*E02B 5/08* (2006.01)
*A61D 99/00* (2006.01)
*A61B 10/02* (2006.01)

(52) U.S. Cl.
CPC ............... *A61D 99/00* (2013.01); *A61B 10/02* (2013.01)

(58) Field of Classification Search
CPC ..................................................... A01K 63/00
See application file for complete search history.

(56) References Cited

U.S. PATENT DOCUMENTS 8,282,836 B2 * 10/2012 Feher .................. E02B 9/04
210/159

OTHER PUBLICATIONS

Nietzel et al. Laboratory studies on the effects of shear on fish, 2000, pp. 1-73.*
USGS, Application of environmental DNA for inventory and monitoring of aquatic species, Jan. 2013, pp. 1-4.*
Sebastien Cadieux, Francois Lalonde, Francois Michalid, Intelligent System for Automated Fish Sorting, and Counting, 6 pages, Intelligent Robots and Systems, 2000. (IROS 2000). Proceedings. 2000 IEEE/RSJ International Conference Oct. 31, 2000 (vol. 2), Takamatsu.
Robin Tillett, Nigel McFarlane; Jeff Lies, Estimating Dimensions of Free-Swimming Fish Using 3D Point Distribution Models, Computer Vision and Image Understanding 79, 123-141 (2000), doi:10. 1006/cviu.2000.0847, available online at http://www.idealibrary. com on Ideal, accepted Feb. 4, 2000, 19 pages, Silsoe Research Institute, United Kingdom.
D.J. White, C. Svellingen, N.J.C. Strachan, Automated Measurement of Species and Length of Fish by Computer Vision, available online at ww.sciencedirect.com accepted Apr. 14, 2008; 8 pages, Fisheries Research 80 (2006) 203-210.
Andrew Rova, Greg Mori, Lawrence M, Dill, One Fish, Two Fish, Butterfish, Trumpeter: Recognizing Fish in Underwater Video, MVA2007 IAPR Conference on Machine Vision Applications, May 16-18, 2007, 4 pages, Tokyo, Japan.
Jorge Cabrera-Gamez, Modesto Castrillon-Santana, Antonio Dominguez-Brito, Daniel Hernandez-Sosa, Josef Isern-Gonzalez, Javier Lorenzo-Navarro, Exploring the Use of Local Descriptors for Fish Recognition in LifeCLEF 2015, http://berlioz.dis.ulpgc.es/rocsiani, 11 pages, Universidad de Las Palmas Gran Canaria, Spain.
Diego Mushfieldt, Mehrdad Ghaziasgar, James Connan, Fish Identification System, Department of Computer Science University of the Western Cape, Bellville, Department of Computer Science Rhodes University, 6 pages, undated but admitted to be prior art, Grahamstown.
Jia-Hong Lee, Mei-Yi Wu, Zhi-Cheng Guo, A Tank Fish Recognition and Tracking System Using Computer Vision Techniques, Dept. of Information Management, National Kaohsiung First University of Science and Technology, Dept. of Information Management, Chang Jung University, Kun Shan University, Jul. 9-11, 2010, ICCSIT, 5 pages, Taiwan, R.O.C. China.
Bridget Benson, Junguk Cho, Deborah Goshorn, Ryan Kastner, Field Programmable Gate Array (FPGA) Based Fish Detection Using Haar Classifiers, Computer Science and Engineering Department, University of CA, American Academy of Underwater Sciences, Mar. 1, 2009, 9 pages, La Jolla CA.
Jamil Sawas, Yvan Petillot, Yan Pailhas, Cascade of Boosted Classifiers for Rapid Detection of Underwater Objects, School of Engineering and Physical Sciences, Heriot-Watt University, 8 pages, ECUA 2010 Istanbul Conference, Edinburgh, United Kingdom,
Paul Viola, Michael Jones, Rapid Object Detection using a Boosted Cascade of Simple Features, Accepted Conference on Computer Vision and Pattern Recognition, 2001, 9 pages, Mitsubishi Electric Research Labs, Cambridge, MA, One Cambridge Center, Cambridge, MA.

* cited by examiner

*Primary Examiner* — Bin Shen
(74) *Attorney, Agent, or Firm* — Lucian Wayne Beavers; Patterson Intellectual Property Law, P.C.

(57) ABSTRACT

A system is provided for collecting cellular material from fish for subsequent DNA analysis. A channel includes a sample collection zone. A fluid ejector is directed into the sample collection zone. A fluid collector is communicated with the sample collection zone. A controller is configured to coordinate ejection of a fluid jet from the fluid ejector and collection of a fluid sample by the fluid collector. The fluid jet dislodges cellular material such as scales and mucous from the fish. The fluid collector collects that cellular material in a fluid sample for subsequent DNA analysis.

9 Claims, 4 Drawing Sheets

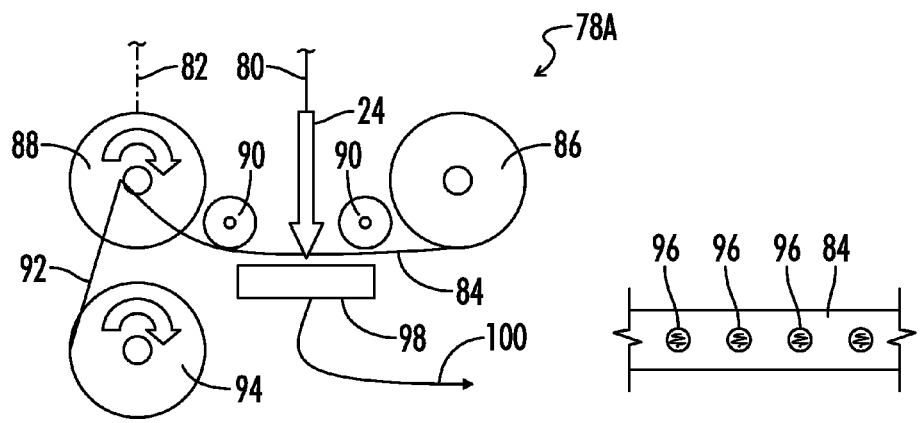
*FIG. 3*  *FIG. 3A*
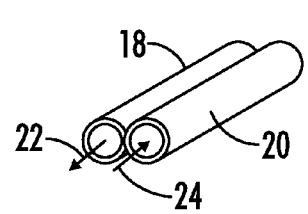  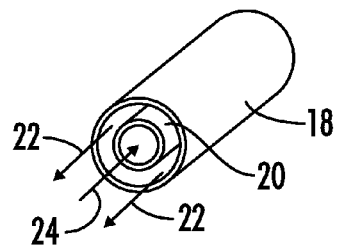
*FIG. 4*  *FIG. 5*
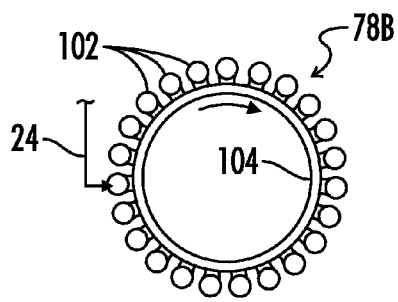  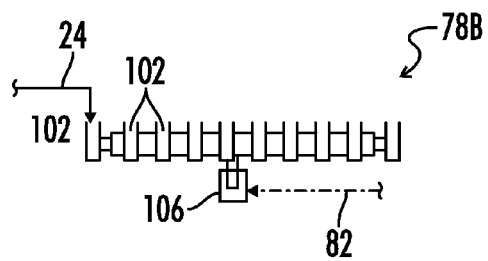
*FIG. 6*  *FIG. 7*

FISH DNA SAMPLER

BACKGROUND OF THE INVENTION

1. Field of the Invention

The invention relates to automated methods and apparatus for collecting samples of fish DNA as migrating fish such as salmon and steelhead pass through a fish ladder or other such defined path.

2. Description of the Prior Art

The study of fish populations traditionally has involved the capture and examination of individual fish. In addition to being time consuming and expensive, such techniques may be harmful to the fish and are accordingly limited in their applicability.

There is a continuing need for improved techniques that allow collection of genetic samples for study of a fish population while reducing any detrimental impact on the fish.

SUMMARY OF THE INVENTION

In one embodiment a method is provided of collecting cellular material from fish, the method may include the steps of:
(a) providing a channel through which a fish may pass;
(b) impacting the fish with a jet of fluid from a fluid ejector and dislodging cellular material from the fish as the fish passes through the channel; and
(c) collecting the cellular material with a fluid collector.

In another embodiment an apparatus is provided for collecting cellular material from fish, comprising a channel including a sample collection zone, a fluid ejector directed into the sample collection zone, a fluid collector communicated with the sample collection zone, and a controller configured to coordinate ejection of a fluid jet from the fluid ejector and collection of a fluid sample by the fluid collector.

In any of the above embodiments the presence of a fish in proximity to the ejector may be automatically sensed, and the ejection of a fluid jet to dislodge a sample of cellular material, and the collection of a fluid sample including the cellular material may be performed automatically in response to sensing the presence of the fish.

In any of the above embodiments the cellular material may be collected by collecting a water sample containing the cellular material.

In any of the above embodiments the cellular material may be collected by filtering water containing the cellular material through a filter medium and collecting the cellular material on the filter medium.

In any of the above embodiments data representative of fish size may be collected and recorded and correlated with the data regarding the cellular material.

In any of the above embodiments after collecting a sample of cellular material, the fluid ejector and fluid collector may be cleared by flowing fluid therethrough.

In any of the above embodiments the ejected fluid used to dislodge the sample of cellular material from the fish may be either water or air.

In any of the above embodiments the collection of the cellular material is preferably performed without contacting the fish other than with the jet of fluid.

In any of the above embodiments, after collection, DNA analysis may be conducted on the cellular material.

Numerous objects features and advantages of the present invention will be readily apparent to those skilled in the art upon a reading of the following disclosure when taken in conjunction with the accompanying drawings.

BRIEF DESCRIPTION OF THE DRAWINGS

FIG. 3 is a schematic illustration of one embodiment of a sample collection and storage system.

FIG. 3A is a schematic view of the filter medium of FIG. 3, with samples of cellular material shown on the filter medium.

FIG. 4 is a schematic perspective illustration of one embodiment of the ejector and collector tubes utilized to collect a fluid sample.

FIG. 5 is a schematic perspective view of a second embodiment of the fluid ejector and collector tubes utilized to collect a fluid sample.

FIG. 6 is a schematic plan view of an alternative embodiment of a fluid collection and storage system.

FIG. 7 is a schematic elevation view of the fluid collection and storage system of FIG. 6.

DETAILED DESCRIPTION

A system is provided which will allow the collection of cellular material sufficient for DNA sampling from a fish as the fish passes through a defined channel. For example, when salmon are migrating upstream to spawn, the collection system described herein may be placed in a fish ladder. The system provides fluid jets for impacting one or the other side of each fish such that sufficient cellular material such as scales and mucous is dislodged from the fish and subsequently collected in a water sample. The cellular material may later be subjected to DNA analysis and the results of that analysis correlated with other information collected regarding the individual fish specimen from which the sample was collected. The automation of such data collection provides vast improvements in the ability to study a defined fish population such as a particular salmon species known to return periodically to a given river.

Figure 1:
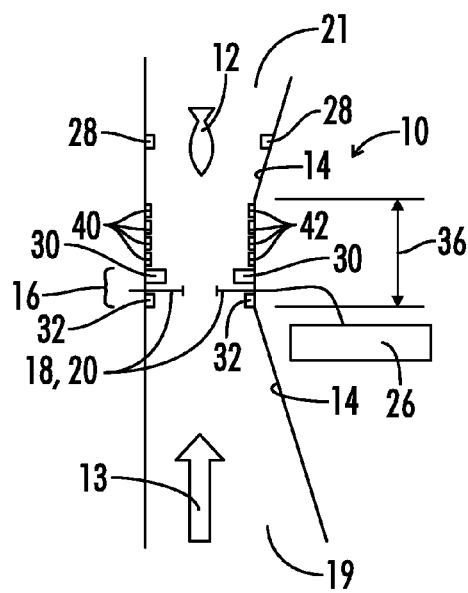
FIG. 1 is a schematic plan view of the apparatus for collecting cellular material from fish.

Referring now to FIG. 1, an apparatus 10 is schematically illustrated for collecting cellular material from fish 12. The apparatus 10 includes a channel 14 including a sample collection zone 16 defined in the channel 14. A fluid ejector 18 and fluid collector 20 are communicated with the sample collection zone. The direction of water flow is indicated by the arrow 13 which will typically be opposite to the direction of travel of the fish 12 as indicated by the orientation of the fish 12 swimming upstream. The channel 14 includes side walls 15 and 17, and has an upstream end 19 and a downstream end 21. The entrance and exit to the channel 14 may be tapered as schematically illustrated in FIG. 1.

There preferably are a plurality of fluid ejectors 18 and a plurality of associated fluid collectors 20. The ejectors and collectors may be provided in pairs, with each pair including one ejector 18 and one collector 20. Additionally, the fluid ejector and collector pairs 18, 20 may be provided on both sides of the channel 14 as schematically illustrated in FIG. 1.

Figure 2:
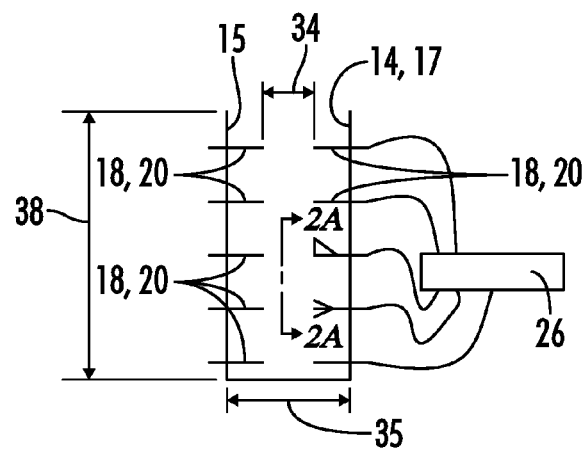
FIG. 2 is a schematic end view of the apparatus of FIG. 1.

The pairs of tubes 18, 20 are vertically spaced from each other as seen in FIG. 2 and extend from at least one of the side walls 15 and 17. The ejector and collector tube pairs 18 may be oriented in a slightly downstream direction so as to minimize the wrapping of debris from the stream on the tubes.

The flexible tubing from which the tubes 18 and 20 are formed may have small balls or other configurations on the end to avoid sharp physical contact with the fish 12 if the fish inadvertently engages the tubes 18, 20.

Furthermore, as schematically illustrated in FIG. 2, there preferably are a plurality of vertically spaced fluid ejector and collector pairs 18, 20 arranged throughout the height of the channel 14. This will allow a proper one of the ejector and collector pairs 18, 20 to be utilized based upon a detected position and proximity of a fish 12 passing through the channel 14.

As shown in FIG. 2 the tube assemblies 18, 20 preferably extend from both walls of the channel 14 and include vertical rows of tube assemblies of sufficient length, for example three or so inches each, such that at least one tube assembly on either side of the fish is within an inch or so of at least one side of the passing fish. The dimensions of the channel 14 are dependent in part upon the expected dimensions of the fish to be studied. For example, a proposed system for the study of Pacific salmon having a typical length of 20 to 30 inches, and a typical weight of 20 to 30 pounds, may utilize a channel 14 having a channel width 35 of approximately 12 inches in the collection zone 16 with the tube assemblies 18, 20 extending approximately three inches into the channel 14 from each side thus providing a gap 34 between the tube assemblies of approximately 6 inches. This provides a scenario wherein the fish should pass within an inch or so of at least one of the ejector and collector tube pairs 18, 20. Testing has shown, for example, that adequate DNA samples can be collected with the ejector/collector tubes spaced as much as 2.5 inches from the fish, at a water flow rate of up to 5 ft/sec through the channel. The narrow portion of the channel 14 may have a length 36 of several feet long. A height 38 of the channel 14 would be determined by water flow requirements for the particular installation.

The tubing 18, 20 as illustrated is arranged for collection of cellular material samples from the sides of the fish. Optionally, the tubing could extend upward from the bottom of the channel 14 for collection of cellular material from the lower body portion of a fish traveling near the bottom of the channel 14.

Two possible examples of the manner of construction of the fluid ejector and collector pairs 18, 20 are schematically illustrated in FIGS. 4 and 5. In both cases the fluid ejector 18 and collector 20 are preferably formed from flexible tubing extending into the channel 14.

As shown in FIG. 4, one embodiment of a fluid ejector and collector pair 18, 20 involves side-by-side conduits. Conduits or tubes 18 and 20 may be conjoined.

As shown in FIG. 5, another embodiment of a fluid ejector and collector pair 18, 20 includes concentrically arranged tubing wherein the ejector 18 is concentrically received about the collector tube 20.

In each of the two cases, a fluid jet 22 of water or air is provided to impact the fish 12 and dislodge a sample of cellular material which is collected by collecting a water sample immediately adjacent the point of impact of the jet 22, which water sample is schematically indicated by the arrows 24 in FIGS. 4 and 5. If air is used as the fluid medium for the fluid jet 22, then the cellular sample may be attached to resulting bubbles via the surface tension of the bubbles.

When utilizing a side-by-side pair of fluid ejector and collector tubes 18, 20 as seen in FIG. 4, the ejector tube 18 is preferably located upstream of the collector tube 20. Thus, for both the embodiment of FIG. 4 and the embodiment of FIG. 5, the collector tube 20 may be described as being located at least in part downstream from the fluid ejector tube 18.

Figure 2A:
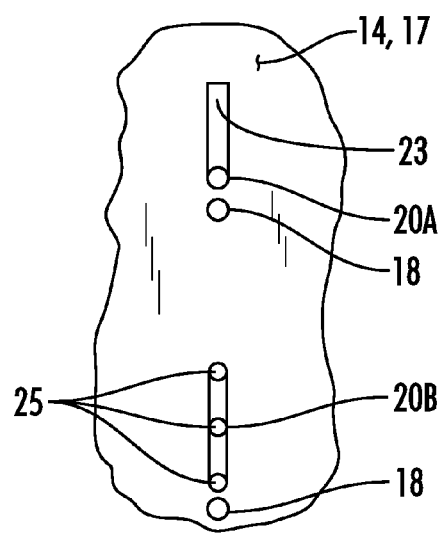
FIG. 2A is a schematic elevation view taken along line 2A-2A of FIG. 2 showing two optional end constructions for the collector tubes.

FIG. 2A also shows two alternative constructions for the end portions of the collector tubes 20. In the upper portion of FIG. 2A a modified collector tube is indicated as 20A and it includes an end piece having a thin vertically elongated inlet opening 23. In the lower portion of FIG. 2A a modified collector tube is indicated as 20B and it is branched to provide three inlet openings 25. In both modified collector tubes 20A and 20B the modified inlet openings may increase the DNA collection because it has been observed in testing that the reflected fluid/cellular material from the fish tends to spread vertically.

Figure 8:
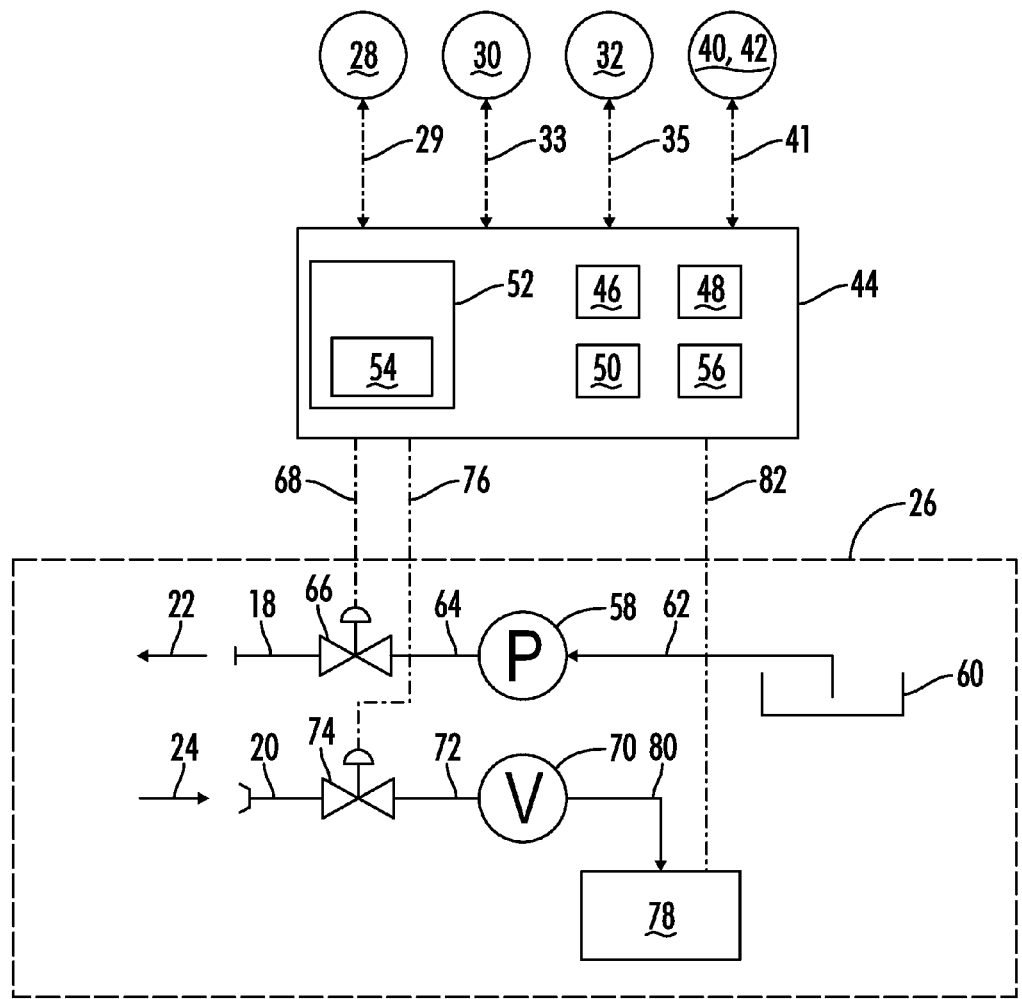
FIG. 8 is a schematic illustration of a controller and associated inputs and outputs for controlling the collection of DNA samples and associated data.

Referring again to FIG. 1, an ejector/collector system 26 is schematically illustrated and is connected to the various ejectors 18 and collectors 20. Further details of construction of the ejector/collector system 26 are shown in FIG. 8.

Also schematically illustrated in FIG. 1 are a number of sensing components which will be utilized to provide automated control of the system.

As the fish 12 moves into the channel 14 from downstream, a first sensor 28 detects the initial presence of the fish 12 entering the channel 14. The sensor 28 may be referred to as a presence sensor, and there may be sensors 28 on either or both sides of channel 14. The presence sensor 28 may be a video camera and associated motion sensing software. A signal from the presence sensor 28 may be utilized to activate the other components of the system.

The presence of a fish entering the channel 14, as detected by sensor 28, will initiate a high frequency acoustic transducer 30, which may include arrays of such transducers on either side of the channel 14. The acoustic transducers 30 may for example be similar to those commonly used in commercial fish locating sonar and may be utilized to detect the location of the fish 12 so as to determine when the fish 12 is in an appropriate position relative to one of the ejector and collector tube pairs 18, 20 so as to initiate a timely collection of a sample. As previously noted the tube assemblies 18, 20 may be vertically spaced as shown in FIG. 2 such that the fish 12 will be in proximity of at least one tube assembly 18, 20 on one or the other side of channel 14 as the fish 12 passes through the channel 14.

Other instrumentation placed near the collection zone 16 may be utilized to collect additional data regarding the fish 12. One aspect of such additional instrumentation can include cameras 32 positioned near the tube assemblies 18, 20. This allows automatic determination and recording of phenotypic information such as fish size, damage morphology, fin clipping and the like. It also allows for viewing of the fish 12 during the cellular sample collection process. The observation cameras 32 may be high speed cameras such that the impact of the fluid jet and dislodgement of cellular material can be observed for the purposes of verifying proper operation of the system and/or subsequent modifications and improvements to the operational parameters.

As an alternative to the cameras 32, or optionally in addition to the cameras 32, an array of LEDs 40 on one side of the channel 14 and photodiodes 42 on the other side of the channel 14 arranged in an array along the length of the channel 14 may be used for providing an indication of the length of the fish 12. It will be understood that there preferably will be a vertically spaced set of such arrays along the height 38 of channel 14 similar to the vertically spaced sets of ejector and collector tubes 18, 20. Additionally, the LED array 40 and photodiode array 42 may be utilized instead of or in addition to the sensors 18 as a presence sensing technology.

The acoustic transducers 30 may also function as proximity sensors 30 configured to detect the presence of a fish 12 in the sample collection zone 16. More particularly, the proximity sensors 30 may determine which of the ejector tube and collector tube pairs 18, 20 should be utilized to collect the sample of cellular material. As previously noted, depending upon the arrangement of the various instrumentation, cameras such as 28 and 32 and/or LED and photodiode arrangements 40, 42 may be utilized as proximity sensors. As is further described below, the controller 44 is configured to activate the fluid ejectors 18 in response to a signal from the proximity sensor 30.

Additionally, the array of LED and photodiode arrangements 40, 42 may be used to determine where the fish is located lengthwise within the channel 14. It is preferable that the ejection of fluid occurs behind the head of the fish so that injury to the eyes of the fish by the fluid jet is avoided.

Referring now to FIG. 8, a schematic illustration is there shown providing further details of the ejector/collector system 26, and of a controller 44 configured to coordinate ejection of fluid jets from the fluid ejectors 18 and collection of fluid samples by the fluid collectors 20.

Controller 44 includes a processor 46, a computer readable memory medium 48, a data base 50 and an input/output module or control panel 52 having a display 54.

The term "computer-readable memory medium" as used herein may refer to any non-transitory medium 48 alone or as one of a plurality of non-transitory memory media 48 within which is embodied a computer program product 56 that includes processor-executable software, instructions or program modules which upon execution may provide data or otherwise cause a computer system to implement subject matter or otherwise operate in a specific manner as further defined herein. It may further be understood that more than one type of memory media may be used in combination to conduct processor-executable software, instructions or program modules from a first memory medium upon which the software, instructions or program modules initially reside to a processor for execution.

"Memory media" as generally used herein may further include without limitation transmission media and/or storage media. "Storage media" may refer in an equivalent manner to volatile and non-volatile, removable and non-removable media, including at least dynamic memory, application specific integrated circuits (ASIC), chip memory devices, optical or magnetic disk memory devices, flash memory devices, or any other medium which may be used to stored data in a processor-accessible manner, and may unless otherwise stated either reside on a single computing platform or be distributed across a plurality of such platforms. "Transmission media" may include any tangible media effective to permit processor-executable software, instructions or program modules residing on the media to be read and executed by a processor, including without limitation wire, cable, fiber-optic and wireless media such as is known in the art.

The term "processor" as used herein may refer to at least general-purpose or specific-purpose processing devices and/ or logic as may be understood by one of skill in the art, including but not limited to single- or multithreading processors, central processors, parent processors, graphical processors, media processors, and the like.

The controller 44 receives input data from sensors such as 28, 30, 32, 40 and 42 via communication lines 29, 33, 35 and 41, respectively. Controller 44 similarly may initiate the operation of those sensors by transmitting appropriate signals to those sensors. The controller 44 may also receive other inputs. Based upon the programming 56 the controller 44 may perform all of the functions described herein.

As seen in FIG. 8, the ejector/collector system 26 may include a source 58 of fluid under pressure, which source 58 may be a pump 58. The pump 58 may take fluid from a fluid source 60 via intake line 62 and deliver the fluid under pressure via a discharge line 64 and a control valve 66 to each ejector tube 18. It will be understood that there may be a separate control valve 66 for each ejector tube 18, but only one valve 66 is shown in the schematic drawing of FIG. 8. Opening and closing of control valve 66 may be provided by signals from controller 44 over control line 68. Control valve 66 may be a solenoid actuated valve.

Similarly, the ejector/collector system 26 includes a suction device 70 which may be further described as a vacuum source or low pressure source, connected to collector tube 20 via conduit 72 and control valve 74. The control valve 74 may open and close in response to signals from controller 44 communicated over control line 76. Again, there may be a separate control valve 74 for each collector tube 20. The fluid samples collected through collector tube 20 may be conveyed to a sample collection and storage system 78 via fluid conduit 80. The operation of the sample collection and storage system 78 may be controlled via signals from controller 44 communicated over control line 82. Control valve 74 may be a solenoid actuated valve.

One embodiment of a sample collection and storage system designated as 78A is schematically illustrated in FIG. 3. In the embodiment of FIG. 3, the fluid sample received from fluid collector tube 20 is delivered to the sample collection and storage system 78A via conduit 80.

The system 78A includes a filter medium 84 in the form of an elongated tape of filter material provided from a filter supply spool 86 and stored on a filter take-up spool 88. Movement of the filter tape 84 is defined by a plurality of guide rollers 90. Advancement of the filter tape 90 in an indexing manner may be provided by controlled rotation of the take-up spool 88 in response to signals from controller 44 conveyed over control line 82.

A spacer film tape 92 is provided from a spacer film supply spool 94 and is wound up on take-up spool 88 along with the filter tape 84 so that each layer of filter tape 84 on the take-up spool 88 is spaced from the next layer by the spacer film 92 to prevent cross contamination of DNA samples collected on the filter tape 84.

Thus, when it is desired to collect a sample of cellular material from the fluid sample 24, a clean portion of the filter tape 84 is indexed into position, and the fluid sample 24 flows through the filter tape 84 so that the cellular material contained in the fluid sample 24 is filtered out of the fluid sample and collected on the filter tape 84.

FIG. 3A schematically illustrates a length of the filter tape 84 wherein a series of samples of cellular material 96 taken from sequential fluid samples 24 are collected on the tape 84 in spaced array. The remainder of the fluid sample after the cellular material has been filtered therefrom is collected at 98 and returned to the river or other discharge reservoir via conduit 100. The filter tape 84 may be dried and stored and the cellular material may be extracted at a later date for DNA testing.

An alternative embodiment of a sample collection and storage system is designated as 78B and shown in FIGS. 6 and 7. The fluid collection and storage system 78B includes a plurality of sample containers 102 for receiving and storing the fluid samples 24. In this embodiment, a plurality of such sample containers 102 may be provided on a rotating index wheel 104. Indexing of wheel 104 may be controlled by an appropriate electric motor 106 in response to command signals received from controller 44 via control line 82.

Thus when it is desired to collect a fluid sample 24, the indexing wheel 104 is appropriately positioned to receive the fluid sample 24 in one of the containers 102. Reagents may be added to the water sample to help maintain sample integrity. For example, for genetic analysis, detergent and DNAse inhibitor may be added to lyse the cells and prevent DNA degradation. DNA may be isolated from the water sample at a later time.

Then, appropriate means may be provided for automated sealing of the container 102 as desired.

Either of the sample collection and storage system 78A or 78B can provide for automated sample collection and storage over an extended period of time. For example, using the fluid sample collection technique of system 78B of FIGS. 6 and 7, assuming a 5,000 fish analysis over a 50 day period with an average 10 hour run time per day would result in approximately 100 fish sample collections per day. Thus, a sample collecting rotor 104 with 100 bottles 102 of one inch diameter would require only a 32 inch diameter rotor 104 and would provide a sample container trade out frequency of once per day.

If the filter tape collection system 78A of FIG. 3 is utilized, far more samples can be collected between service intervals for the automated system.

Methods of Operation

The method of using the apparatus 10 may be generally described as providing the channel 14 through which fish 12 may pass. As the fish 12 passes through the channel 14, the fish 12 is impacted with a jet 22 of fluid from a fluid ejector 18 to dislodge cellular material 96 from the fish 12 as the fish 12 passes through the channel 14. The cellular material 96 is then collected with a sample collection and storage system such as 78A or 78B. That overall process is more specifically implemented as follows. This implementation is schematically summarized in the flow chart of FIG. 9.

The method may be begin with a step 108 of automatically sensing the presence of a fish 12 in proximity to the ejector tubes 18. That step 108 may in turn be broken down into steps 110 of detecting fish presence within the channel 14 such as via the presence sensor 28, then step 112 of activating the proximity transducers 30 via command signals from controller 44 over control line 33, then step 114 of detecting proximity of the fish 12 to the ejector tubes 18 via the proximity sensors 30.

Once the controller 44 has determined that the fish 12 is in appropriate position relative to one of the pairs 18, 20 of ejector and collector tubes, the controller 44 may send a control signal over control line 68 to the appropriate control valve 66 associated with the appropriate one of the ejector tubes 18 to eject a short burst of fluid jet toward the fish 12 as indicated at step 116. This short pulse of fluid jet may for example have a duration in the range of from 0.01 second to 0.10 second.

Immediately after the fluid jet pulse, the controller 44 sends a second signal via control line 76 to the appropriate control valve 74 associated with the appropriate one of the collector tubes 20 so that the collector tube 20 will suck in a sample of water adjacent the location of impact of the fluid jet 22 on the fish 12 as indicated at block 118.

That fluid sample 24 is then passed via conduits 72 and 80 to the sample collection and storage system 78 wherein the cellular material sample is stored as indicated at block 120.

It is noted that it is important to clean the various fluid passages which have been contacted by the fluid sample 24 during the sample collection process. It is also important to clean the ejector tube 18 immediately adjacent the point of impact of the fluid jet 22 with the fish 12. All of this is so that the test structure is appropriate cleaned between sample taking instances, so that there is no cross-contamination of cellular material from one fish sample to the next. This cleaning can be accomplished by automatic control from controller 44 by pulsing the fluid jet 22 and intake of fluid sample 24 via operation of control valve 66 and 70 when no fish is present adjacent the ejector and collector tube pair 18, 20, thus flushing those tubes of any residual cellular material. This is all indicated at block 122 in FIG. 9.

Figure 9:
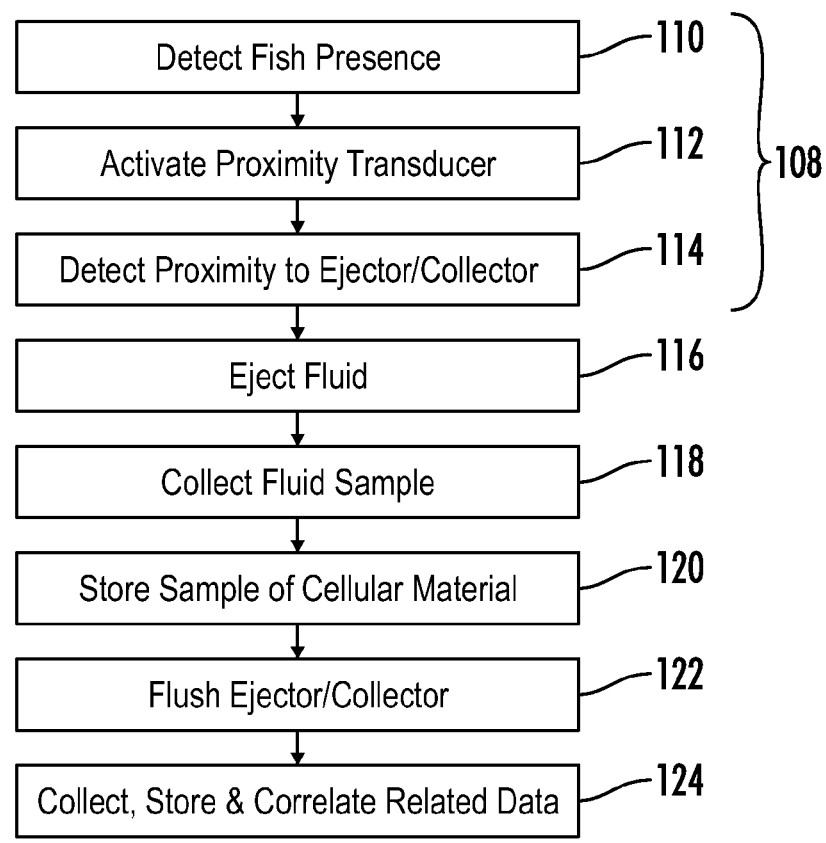
FIG. 9 is a flow chart summarizing the process of collecting cellular material from fish.

As previously noted, during the sample collection process, additional data regarding the sample and the particular fish sample may be collected as indicated at block 124 in FIG. 9. This additional data may include for example the following:
1. video data of the fish and the sampling process;
2. LED/photodiode size detection data;
3. time of data collection;
4. position of fish within ejector/collector array;
5. location of cellular material sample in the sample collection storage system 78.

Thus a system 10 has been provided which allows for automated collection of cellular material samples for DNA testing without contacting the fish 12 during the testing procedure.

The utilization of motion sensing software or presence detector technology 28 to initiate sample taking allows the minimization of energy consumption by the apparatus 10 and minimizes the introduction of acoustic energy into the fish ladder water flowing through the channel 14.

Further refinements may include the addition of pattern recognition software to allow the apparatus 10 to distinguish between one fish passing through the channel 14 as contrasted to two or more fish attempting to pass through the channel 14 at one time. The system may discriminate to choose not to collect cellular material samples when more than one fish is present in the channel 14.

The controller 44 may also be configured via software 56 to vary the strength and/or duration of the fluid pulse 24 as a function of the distance of the fish 12 from the ejector tube 18 as determined by the proximity sensor 30.

The controller 44 may also be configured via software 56 to detect distinctive physical characteristics of the fish 12 such as the presence of a clipped fin via image processing software.

Thus it is seen that the methods and apparatus of the present invention readily achieve the ends and advantages mentioned as well as those inherent therein. While certain preferred embodiments of the invention have been illustrated and described for purposes of the present disclosure, numerous changes in the arrangement and construction of parts and steps may be made by those skilled in the art, which changes are encompassed within the scope and spirit of the present invention as defined by the appended claims.

What is claimed is:
1. An automated method of collecting cellular material from living fish, comprising:
   (a) providing a channel through which a fish may pass;
   (b) impacting the fish with a jet of fluid from a fluid ejector after automatically sensing a presence of the fish in proximity to the ejector and dislodging cellular material from the fish as the fish passes through the channel; and
   (c) collecting the cellular material with a fluid collector;

wherein steps (b) and (c) are automatically performed in response to the automatic sensing of the presence of the fish.

2. The method of claim 1, wherein:
step (c) comprises collecting a water sample containing the cellular material.

3. The method of claim 1, wherein:
step (c) comprises filtering water containing the cellular material through a filter medium and collecting the cellular material on the filter medium.

4. The method of claim 1, further comprising:
collecting and recording data representative of fish size and correlating the data with the cellular material.

5. The method of claim 1, further comprising:
after step (c), clearing the fluid ejector and fluid collector by flowing fluid therethrough, and then repeating steps (b) and (c) for another fish.

6. The method of claim 1, wherein:
in step (b) the fluid is water.

7. The method of claim 1, wherein:
in step (b) the fluid is air.

8. The method of claim 1, wherein:
steps (b) and (c) are performed without contacting the fish.

9. The method of claim 1, further comprising:
conducting DNA analysis of the cellular material.

* * * * *